July 31, 1956
H. M. TIRET
Plant Pat. 1,501
FUCHSIA PLANT
Filed Sept. 28, 1955
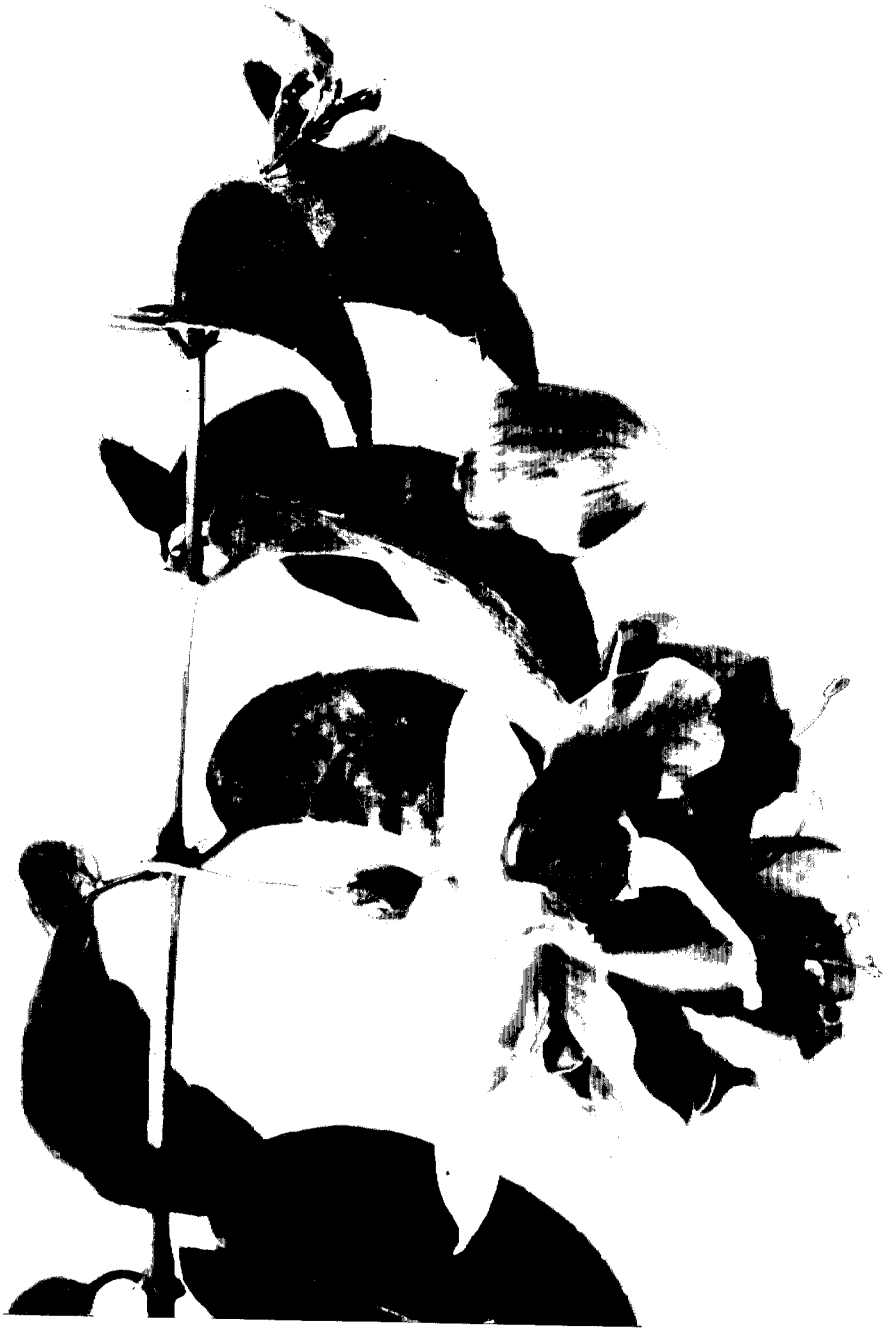

United States Patent Office

Plant Pat. 1,501

Patented July 31, 1956

1,501

FUCHSIA PLANT

Horace M. Tiret, San Francisco, Calif.

Application September 28, 1955, Serial No. 537,314

1 Claim. (Cl. 47—60)

This invention relates to a new and improved fuchsia plant, the principal new and different characteristic of which is the exceptional size and color of the flower, in combination with the abundance of blooms and vigorous habit of growth. The plant was derived as a hybrid from seedlings (unpatented) not introduced to the trade, namely, 4–8–5 (female), and 5–25–7 (male), the figures representing applicant's own breeding symbols. The fuchsia plant is distinguished principally by its vigorous, upright habit of growth, together with the exceptional size and color of the flower, in combination with the abundance of blooms which tend toward a symmetrical form, this combination not previously existing in any other fuchsia plant. The plant has been asexually reproduced at Palo Alto, California, by cuttings which retain the characteristics of the parent fuchsia.

The plant is an upright variety and grows vigorously, throwing dense branches in a vertical direction. When the plant blooms, the buds open into an abundance of blooms, all combined to give it a symmetrical effect. When the flower first opens, the petals are heliotrope (British Horticultural Color Chart 636–2). At full maturity the main petals are mauve (British Horticultural Color Chart 633), while the outer petals are marbled at the base and colored phlox pink (British Horticultural Color Chart 625–1). The flower has no fragrance. It has a long blooming season.

In the accompanying drawing, the figure shows a typical branch tip, the drawing representing approximately actual size.

A detailed description of this new variety of fuchsia plant follows:

*Habit of growth.*—Vigorous, upright growth, with the branches close together, quite dense, and tending to grow in a vertical direction. The flowers are equally spaced among the foliage and are exceptionally large, considering the quantities of blooms produced.

*Foliage.*—The foliage is medium large and dark green. The branches are dark, reddish brown. The mature leaf is approximately 2¾″ in length and 1⅞″ in width, at the widest part, measured at maturity. The veining of the leaf, and the serrating of the edge are both medium. The leaf is somewhat crinkly in appearance, with the underside a lighter green than the top side.

*Flower.*—The flower is double. The petals number approximately twenty-one. They form an exceptionally large, loose, flaring corolla. When the flower first opens, the main petals are heliotrope (British Horticultural Color Chart 636–2), while the fully matured main petals are colored mauve (British Horticultural Color Chart 633). The outer petals of the flower (both mature and immature) are marbled at the base and colored phlox pink (British Horticultural Chart 625–1). The diameter of the open flower is approximately 3⅝″, measured at maturity. The large center petals measure approximately 2″ in length and 2″ in width, when fully spread out, measured at maturity. The petals are smooth and soft in appearance.

*Ovary.*—Clear green in color. Length ½″, width at widest point ⅜″, measured at maturity.

*Sepals.*—Sepals are four in number. They measure 1¾″ in length, and 1″ in width, measured at the widest point, at maturity. The sepals are broad and horizontally recurved when the flower is fully mature. The texture of the underside is smooth, crepe-like, and the outer side is smooth and satiny.

*Pistil.*—The style is approximately 3¼″ in length from the tip of the ovary, and 1/16″ in width, measured at maturity. The color is pale pink. The stigma is white.

*Tube.*—The tube is phlox pink (British Horticultural Color Chart 625–1). The top side is phlox pink (British Horticultural Color Chart 625–2), and the underside is phlox pink (British Horticultural Color Chart 625–1). There is no fading in the sepals or the tube, as the flower matures, and both the tube and the sepals are the same coloring. The tube is short and broad. The length is approximately ½″, and the width is approximately ½″, measured at maturity.

*Stamens.*—The stamens are eight in number. The color is phlox pink, with pink anthers. In form the tube is medium slender and measures approximately 2½″ in length, measured at maturity.

*Parentage.*—Applicant's own seedlings (unpatented) not introduced to the trade, applicant's breeding symbols 4–8–5 (female), and 5–25–7 (male).

It is noted that the foliage and flowers will vary somewhat with the seasons and growing conditions; however, the fuchsia plant is clearly differentiated from others by the exceptional size and unusual color of the flower in combination with the abundance of blooms and vigorous habit of growth. Additional distinctive characteristics are the unusually symmetrical form and the very long growing season of the plant.

Having thus disclosed my discovery, I claim:

The new and distinct variety of fuchsia plant herein described and illustrated, characterized by the exceptional size and unusual color of the flower in combination with the abundance of blooms and vigorous habit of growth, together with the overall symmetrical form.

No references cited.